(12) United States Patent
Green et al.

(10) Patent No.: US 6,548,474 B1
(45) Date of Patent: Apr. 15, 2003

(54) DISUBSTITUTED CYCLOALKANONES AS FRAGRANCE MATERIALS

(75) Inventors: Carter B. Green, Stony Point, NY (US); Tetsuo Nakatsu, Chappaqua, NY (US); Andrew T. Lupo, Jr., Emerson, NJ (US)

(73) Assignees: Takasago International Corporation, Tokyo (JP); Takasago Institute for Interdisiplinary Science Inc., Rockleigh, NJ (US)

( * ) Notice: Subject to any disclaimer, the term of this patent is extended or adjusted under 35 U.S.C. 154(b) by 0 days.

(21) Appl. No.: 09/105,165

(22) Filed: Jun. 26, 1998

(51) Int. Cl.[7] ................................................. A61K 7/46
(52) U.S. Cl. ............................ 512/8; 424/70.1; 510/101; 512/15
(58) Field of Search ...................... 512/15, 8; 424/70.1; 510/101

(56) References Cited

U.S. PATENT DOCUMENTS 3,342,186 A    9/1967   Cook ........................... 131/17

FOREIGN PATENT DOCUMENTS

| DE | 3338853 A | | 5/1984 |
|---|---|---|---|
| EP | 0 016 650 | * | 1/1980 |
| EP | 0504592 A | | 9/1992 |
| EP | 0770671 A | | 5/1997 |
| FR | 2351078 A | | 12/1977 |
| JP | 6080606 | | 3/1994 |
| WO | 9205713 | | 4/1992 |

OTHER PUBLICATIONS

"Synthesis of a Potential Steroid Intermediate by Anionic Oxy–Cope Rearrangement", Tetrahedron Letters, vol. 30, No. 33 pp. 4427–4428, 1989.*

"Synthesis of Linearly Fused Tricyclic Compounds Via Thermal Oxy–Cope Rearrangement", Tetrahedron, vol. 52, No. 2, pp. 7737–7744, 1996.*

Qi et al., "Alkylation of 2–cyclopentylidenecyclopentanone", *Hecheng Huaxue*, 4(4):296–299 (1996). (in Chinese).

Qi et al., "Synthesis of 2–(1–cyclopentenyl)–2–alkylcyclopentanone Mannich base hydrochlorides and studies on their anticancer and antiinflammatory activities", *Zhongguo Yaowu Huaxue Zazhi*, 5(4):235–41 (1995). (In Chinese).

Qi et al., "Synthesis and potential antineoplastic activity of αφ(1–cyclopentenyl)cyclopentanone derivatives—a new family of anticancer agents", *Chin. Chem. Lett.* 6(10):847–50 (1995).

Koppes et al., "Photochemistry of β,φenones. 9. Mechanistic photochemical studies on the 1,3 acyl shift and oxa–di–πφmethane rearrangement of two β,γ,γ,δ–dienones", *Neth. Recl. Trav. Chim. Pays–Bas*, 104(10):272–6 (1985).

Van der Veen et al., "Photochemistry of β,γφenones—VIII. On the remarkable photostability of some β,γ,β,γ–dienones and the 1,3–acyl shift photoreactivity of two β,γβ,γ–dienones", *Neth. Tetrahedron* 41(3):585–94 (1985).

(List continued on next page.)

Primary Examiner—Jill Warden
Assistant Examiner—Monique T. Cole
(74) Attorney, Agent, or Firm—Darby & Darby (57) ABSTRACT

Disubstituted cycloalkanones are prepared from one of 2-cyclopentylidenecyclopentan-1-one, 2-cyclohexylidenecyclohexan-1-one, 2-cyclopentylidenecyclohexan-1-one, or 2-cyclohexylidenecyclopentan-1-one. The resulting compounds were analyzed for their odor characteristics. The different compounds exhibited varied odor characteristics, which were not predictable from the structures of the compounds. The compounds are useful in the preparation of fragrance compositions and products formed from same.

11 Claims, 2 Drawing Sheets

OTHER PUBLICATIONS

Buys et al., "Photochemistry of αφoxo oxime ethers. 8 Steric control in the photochemical E–Z isomerization of some (over)crowded αφoxo oxime ethers", *Neth. Recl. Trav. Chim. Pays–Bas* 104(1):19–24 (1985).

Van der Veen et al., "Temperature–dependent alkylation of γφpheny β, γφunsaturated acid and ester systems in hexamethyl–phosphoric triamide–tetrahydrofuran solutions using lithium diisopropylamide", *Neth. J. Org. Chem* 50(3):342–6 (1985).

Coffin et al., "Photochemical studies on the mechanism of the oxadi–πφmethane rearrangement. An example of a stereospecific rearrangement", *J. Amer. Chem. Soc.* 101(12):3261–72 (1979).

Bakuzis et al., "Acid–catalyzed ketone rearrangements. Synthesis of decalins and spiro[4,5]decanes", *J. Org. Chem.* 39(16):2427–9 (1974).

Carlson et al., "Synthetic organic photochemistry. Photochemical approach to hydroazulenes by photolysis of a β,γφunsaturated ketone", *J. Chem. Soc., Chem. Commun.* 14:501–2 (1973).

Van der Veen et al., "Electrophilic substitution of β, γφunsaturated esters and ketones using phenyl vinyl sulfoxide as a vinyl cation synthon", *Neth. J. Chem. Soc.* 4:661–8 (1985).

Wang et al., "Synthesis of a vegetable flavor fragrance", *Shiyou Huagong Gaodeng Xuexiao Xuebao* 10(4):34–35, 43 (1997) (in Chinese).

Nakano et al., "Cross–condensation reactions of cycloalkanones with aldehydes and primary alcohols under the influence of zirconocene complexes", *J. Org. Chem.* 52(11):2239–44 (1987).

Yasuda et al., "The effect of alkyl substituents on the mode of reactions of organozinc and organoaluminum compounds with ketones", *Nippon Kagaku Kaishi* 3:317–23 (1985) (in Japanese).

Sepiol et al., "Elimination of the nitrile group from carbocyclic o–hydroxynitriles", *Synthesis* 4:290–2 (1979).

Mekhtiev et al., "Synthesis of cycloalkenylcyclanones", *Azerb. Khim. Zh.* 5–6:93–7 (1971) (in Russian).

Negishi et al., "Stereoselective synthesis of exocyclic alkenes via zirconium–promoted alkyl–diene coupling", *J. Org. Chem.* 54(26):6014–16 (1989).

Mekhtiev et al., "Relation of odor to the structure of some alkylcyclanones", *Dokl. Akad. Nauk Az. SSR* 32(12):46–52 (1976) (in Russian).

Reetz et al., "Lewis acid mediated αφthioalkylation of ketones", *Synth. Commun.* 11(4):315–22 (1981).

Maradyn et al., "The photochemical cycloaddition reaction of 2–cyclohexenone with alkenes: trapping of triplet 1,4–biradical intermediates with hydrogen selenide", *Tetrahedron Lett.* 35(44):8107–10 (1994).

Suleimanova et al., "Free–radical addition of cyclanones to unsaturated hydrocarbons", *Azerb. Khim. Zh.* 3:42–6 (1979) (in Russian).

Opdyke, D.L.J., "Fragrance raw materials. 2–cyclohexanone", *Food Cosmet. Toxicol.* 12(3):399 (1974).

Moldovanskaya et al., "Perfumes from alkylphenols XVIII. Synthesis of 2–and 4–cyclohexylcyclohexanones", *Tr. Vses. Nauch.–Issled.Inst. Sin. Natur. Dushist. Veshchestv.* 9:77–81 (1971).

Schweisheimer, W., "Aromatic chemical products used in cosmetics—aromas and odors are being used more and more", *Parfum., Cosmet., Savons* 9(8):363–7 (1966) (in French).

Arctander S., "Perfume and Flavor Chemicals (Aroma Chemicals).", Steffen Arctander, 1969, p. 789.

R.H. vanderVeen and H. Cerfontain, "on the remarkable photostability of some dienones and the 1,3–acyl shift photoreactivity of two dienones", Tetrahedron, v.41, No. 3, 1985, pp. 585–594.

Chemical Abstracts, v. 127, No. 4, Jul. 28, 1997, abstract No. 50306r, Qi et al., "Alkylation of 2–cyclopentylidenecyclopentanone", Hechen Huaxue, v.4, No. 4, 1996, pp. 296–299.

European Search Report of EP 99 10 9471, May 25, 2000.

\* cited by examiner

DISUBSTITUTED CYCLOALKANONES AS FRAGRANCE MATERIALS

BACKGROUND OF THE INVENTION

The present invention relates to disubstituted cycloalkanones for use as fragrance materials. More particularly, the present invention relates to disubstituted cycloalkanones of the following general formula (I) or (II):

wherein $R^1$ is a straight-chain or branched saturated or unsaturated hydrocarbon group having between 1 and 6 carbon atoms, and m and n are each either 1 or 2.

Disubstituted cycloalkanones are prepared by alkylation of cycloalkylidenecycloalkanones (Qi et al., Hecheng Huaxue 4(4):296–299 (1996)). Disubstituted cycloalkanones are of interest as potential antiinflammatory compounds and anticancer compounds. Qi et al. synthesized 2-(1-cyclopentenyl)-2-alkylcyclopentanone Mannich base hydrochlorides, and performed studies on their anticancer and antiinflammatory properties (Zhongguo Yaowu Juaxue Zazhi 5(4):235–42 (1995)). They showed that some species had significant antitumor activity against cultured cancer cell lines, and others showed significant antiinflammatory activity comparable to that of indomethacin. In a separate work, the same authors synthesized α,β-unsaturated and β-aminomethylcyclopentanones containing α-(1-cyclopentenyl) and showed these compounds exhibited significant levels of anticancer activity in vitro against cultured cancer cell lines (Chin. Chem. Lett. 6(10):847–850 (1995)).

Various monosubstituted cycloalkanones have been investigated for use as fragrances. In particular, 2-cyclohexylcyclohexanone (reviewed in Food Cosmet. Toxicol. 12(3):399 (1974)) and 2-cyclopentenones (Ger. Offen. DE 83-3338853) have been prepared for use as fragrances. In addition, 2-cyclopentylcyclopentanone was used in preparation of a dentrifice, a soap, and a fragrance or flavoring composition giving a jasmine-like smell (European Patent EP 16650 801001). Furthermore, Japanese Patent Publication JP 82-230558 discloses the use of δ-cyclopentyl-δ-lactone in perfume preparations.

Mekhtiev et al. studied the structure/odor relationships among selected monosubstituted cycloalkanones (Dokl. Akad. Nauk Az. SSR 32(12):46–52 (1976)). They concluded that introduction of an n-alkyl group at the α-position in a cyclopentanone ring caused a fatty odor increasing in intensity from methyl to propyl, and a strong jasmine scent for C4 to C7 groups. Cyclohexanone derivatives had a weaker jasmine scent than their cyclopentanone analogs. Branched amyl- and hexylcyclopentanones with geminal terminal methyl groups also gave a jasmine scent, with strong fruity or woody overtones. Substitution of a methyl or ethyl group at the α'-position of the cyclopentanone ring carrying an n-alkyl group weakened the jasmine scent, and increased the fruity tones.

While monosubstituted and disubstituted cycloalkanones are known in the art, the use of di substituted cycloalkanones as fragrance materials has not been investigated. More particularly, the use of disubstituted cycloalkanones as fragrance materials for consumer products has not been investigated.

OBJECTS AND SUMMARY OF THE INVENTION

It is an object of the present invention to provide disubstituted cycloalkanones for use as fragrance material.

It is another object of the present invention to provide disubstituted cycloalkanones suitable for use as fragrance materials in commercial consumer products, such as cleaning materials, perfumes, and personal hygiene products.

Briefly stated, di substituted cycloalkanones are prepared from one of 2-cyclopentylidenecyclopentan-1-one, 2-cyclohexylidenecyclohexan-1-one, 2-cyclopentylidenecyclohexan-1-one, or 2-cyclohexylidenecyclopentan-1-one. The resulting compounds were analyzed for their odor characteristics. The different compounds exhibit varied odor characteristics, which are not predictable from the structures of the compounds. The compounds are useful in the preparation of fragrance compositions suitable for use in consumer products.

According to an embodiment of the present invention, a fragrance composition consisting of a disubstituted cycloalkanone of the following general formula (I) or (II):

wherein $R^1$ is a member selected from the group consisting of a straight-chain saturated hydrocarbon group, a branched saturated hydrocarbon group, a straight-chain unsaturated hydrocarbon group, and a branched unsaturated hydrocarbon group, and wherein $R^1$ has between 1 and 6 carbon atoms, and wherein m and n are each either 1 or 2.

The above, and other objects, features and advantages of the present invention will become apparent from the following description read in conjunction with the accompanying drawing.

DETAILED DESCRIPTION OF THE PREFERRED EMBODIMENT

The present invention comprises disubstituted cycloalkanones useful as fragrance materials. The compounds of the present invention are prepared from 2-cyclopentylidenecyclopentan-1-one, 2-cyclohexylidenecyclohexan-1-one, 2-cyclopentylidenecyclohexan-1-one, or 2-cyclohexylidenecyclopentan-1-one. The structural formulae of Embodiments 1 through 11 are shown in FIGS. 2a–2k.

Those skilled in the art will recognize that the specified reagents and conditions indicated in the following embodiments are sufficient but not necessary for the preparation of the materials of this invention with varying degrees of success. In particular, the selection of NaH for base catalysis is one of many that could be chosen from a list including, but not limited to, NaOH, KOH, sodium methoxide or lithium bistrimethysilylamide. In addition, the selection of THF as the solvent is one of many solvents that could be chosen from a list including, but not limited to, diethyl ether, methyl tert-butyl ether, 1,4-dioxane or toluene, that one skilled in the art can determine is compatible with the given reaction conditions. The alkylating agents specified, allyl chloride for Embodiment #1 for example, could also be replaced by other alkyl halides and sulfonates and would be expected by one skilled in the art to give varying degrees of success for the preparation of the materials of this invention.

Preparation of 2-cyclopentylidenecyclopentan-1-one

Figure 1:
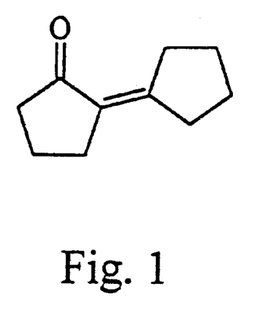
FIG. 1 shows the structural formula of 2-cyclopentylidenecyclopentan-1-one.

To a stirring solution of cyclopentanone (336.5 g, 4.0 moles) in absolute ethanol (500 mL) at room temperature was added KOH (5.6 g, 0.1 mole) in one portion. The reaction was stirred at room temperature for 65 hours. The reaction was determined to be completed by TLC and GC analyses. Hexane was added to the reaction mixture and the layers were separated. The organic layer was washed successively with 10% HCl (aqueous), saturated NaHCO$_3$ (aqueous) and brine. The resulting organic layer was dried with MgSO$_4$, filtered, and concentrated. The brown oil was distilled under vacuum to give 2-cyclopentylidenecyclopentan-1-one (155 g, 52% yield). The structural formula of 2-cyclopentylidenecyclopentan-1-one is shown in FIG. 1.

The CAS registry number is 825-25-2. The molecular formula is C$_{10}$H$_{14}$O, and the molecular weight is 150.22. The boiling point is 80–82° C. at 0.3 mm Hg.

500 Mhz. $^1$H-NMR analysis (in CDCl$_3$) provided the following data: δ1.61–1.71 (m, 4H), 1.83–1.91 (m, 2H), 2.25–2.27 (t, 4H), 2.49 (bs, 2H), 2.73 (bs, 2H).

125 Mhz $^{13}$C-NMR analysis (in CDCl$_3$) provided the following data: δ20.15, 25.30, 27.0, 29.58, 32.61, 34.36, 39.86, 127.94, 158.68, 207.43.

IR analysis provided the following. data (ν$_{max}$(cm$^{-1}$)): 1170(m), 1255(m), 1420(w), 1640(s), 1705(s), 2875(m), 2960(s).

MS analysis provided the following data (m/z): 150 (M$^+$), 135, 121, 107, 91, 84, 79, 67, 51, 39.

Embodiment 1

Preparation of 2-cyclopent-1-enyl-2-prop-2-enylcyclopentan-1-one

To a stirring solution of 2-cyclopentylidenecyclopentan-1-one (62.5 g, 0.417 moles) in dry THF (450 mL) at room temperature under nitrogen, was added NaH (60% oil dispersion, 20.0 g, 0.5 moles) in one portion. The mixture was stirred at room temperature for 30 min and then a solution of allyl chloride (38.3 g, 0.5 moles) in THF (100 mL) was added dropwise over 30 min. When the addition was complete, the reaction was warmed gently to approximately 40° C. It was determined by TLC and GC that the reaction was complete after 18 hours. Water was added to the reaction mixture and the layers were separated, with the organic layer being washed successively with 10% HCl (aqueous), saturated NaHCO$_3$ (aqueous), and brine. The resulting organic layer was dried with MgSO$_4$, filtered, and concentrated. The brown oil was distilled under vacuum to give 2-cyclopent-1-enyl-2-prop-2-enylcyclopentan-1-one (54.5 g, 69.0% yield).

Figure 2A:
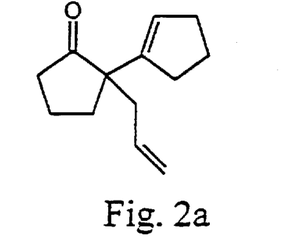
FIG. 2a shows the structural formula of Embodiment 1.

The CAS registry number is 7011-72-5. The molecular formula is C$_{13}$H$_{18}$O, and the molecular weight is 190.28. The boiling point is 84° C. at 0.4 mm Hg. The structural formula of 2-cyclopent-1-enyl-2-prop-2-enylcyclopentan-1-one is shown in FIG. 2a.

500 Mhz $^1$H-NMR (in CDCl$_3$): δ1.77–1.88 (m, 5H), 2.08–2.15 (m, 2H), 2.19 (dd, 1H), 2.24–2.36(m, 5H), 2.42 (dd, 1H), 4.98–5.06 (m, 2H), 5.50 (t, 1H), 5.57–5.67 (m, 1H).

125 Mhz $^{13}$C-NMR (in CDCl$_3$): δ19.05, 23.49, 31.80, 32.51, 33.14, 37.88, 39.43, 55.07, 117.60, 127.15, 134.48, 142.70, 219.17.

IR (ν$_{max}$(cm$^{-1}$)): 920(m), 1000(w), 1150(m), 1640(w), 1740(s), 2960(s), 3080(w).

MS (m/z): 190 (M$^+$), 172, 161, 149, 134, 119, 105, 91, 79, 65, 55, 39.

Embodiment 2

Preparation of 2-cyclopent-1-enyl-2-methylcyclopentan-1-one

The material was prepared as for Embodiment 1, with the exception that after the addition of NaH and subsequent stirring at room temperature for 30 min, the reaction mixture was cooled in an ice-water bath to a temperature between approximately 0–5° C. To the cooled mixture was added an excess of methyl iodide in THF dropwise over 1 hour. When the addition was complete, the solution was allowed to warm to room temperature overnight. It was determined by TLC and GC that the reaction was complete after 18 hours. From 2-cyclopentylidenecyclopentan-1-one (10.0 g, 0.067 moles) 2-cyclopent-1-enyl-2-methylcyclopentan-1-one (1.1 g, 10.0% yield) was obtained.

Figure 2B:
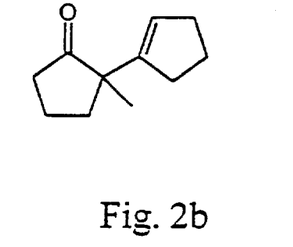
FIG. 2b shows the structural formula of Embodiment 2.

The CAS registry number is 43011-75-2. The molecular formula is C$_{11}$H$_{16}$O, and the molecular weight is 164.24. The boiling point is 38° C. at 0.4 mm Hg. The structural formula of 2-cyclopent-1-enyl-2-methylcyclopentan-1-one is shown in FIG. 2b.

500 Mhz $^1$H-NMR (in CDCl$_3$): δ1.14 (s, 3H), 1.66–1.71 (m, 1H), 1.79–1.87 (m, 4H), 2.16–2.30 (m, 7H), 5.40 (m, 1H).

125 Mz $^{13}$C-NMR (in CDCl$_3$): δ19.04, 21.56, 23.37, 31.64, 32.48, 36.48, 37.51, 51.30, 125.72, 144.69, 220.65.

IR (ν_max(cm⁻¹)): 1060(m), 1160(m), 1370(w), 1455(m), 1630(w), 1740(s), 2875(s), 2960(s).

MS (m/z): 164 (M⁺), 149, 146, 135, 131, 121, 108, 93, 79, 67, 39.

Embodiment 3

Preparation of 2-cyclopent-1-enyl-2-ethylcyclopentan-1-one

This material was prepared as described for Embodiment 1, except that ethyl bromide was used in place of allyl chloride. After the addition of ethyl bromide, the reaction was stirred overnight at room temperature. It was determined by TLC and GC that the reaction was complete after 20 hours. From 2-cyclopentylidenecyclopentan-1-one (10.0 g, 0.067 moles) 2-cyclopent-1-enyl-2-ethylcyclopentan-1-one (3.1 g, 26.0% yield) was obtained.

Figure 2C:
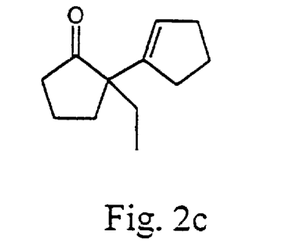
FIG. 2c shows the structural formula of Embodiment 3.

The CAS registry number is 100519-76-4. The molecular formula is $C_{12}H_{18}O$, and the molecular weight is 178.27. The boiling point is 50° C. at 0.2 mm Hg. The structural formula of 2-cyclopent-1-enyl-2-ethylcyclopentan-1-one is shown in FIG. 2c.

500 Mhz ¹H-NMR (in CDCl₃): δ0.75 (t, 3H), 1.36–1.42 (m, 1H), 1.68–1.88 (m, 6H), 2.08–2.34 (m, 7H), 5.49 (m, 1H).

125 Mhz ¹³C-NMR (in CDCl₃): δ9.12, 19.08, 23.44, 27.65, 31.78, 32.51, 33.28, 37.98, 55.77, 127.05, 142.72, 219.73.

IR (ν_max(cm⁻¹)): 1155(m), 1380(w), 1460(m), 1630(w), 1740(s), 2875(s), 2960(s).

MS (m/z): 178 (M⁺), 163, 160, 149, 121, 107, 93, 79, 67, 41.

Embodiment 4

Preparation of 2-cyclopent-1-enyl-2-(2-methylprop-2-enyl)cyclopentan-1-one

The material was prepared as in Embodiment 1, except that methallyl chloride was used in place of allyl chloride. When the addition of methallyl chloride was complete, the reaction was warmed gently to approximately 55° C. It was determined by TLC and GC that the reaction was complete after 7 hours. From 2-cyclopentylidenecyclopentan-1-one (80.1 g, 0.534 moles) 2-cyclopent-1-enyl-2-(2-methylprop-2-enyl)cyclopentan-1-one (89.3 g, 81.9% yield) was obtained.

Figure 2D:
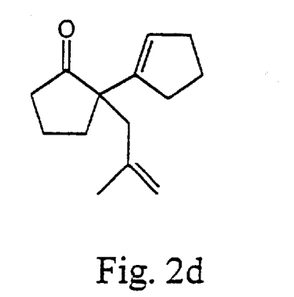
FIG. 2d shows the structural formula of Embodiment 4.

The molecular formula is $C_{14}H_{20}O$, and the molecular weight is 204.31. The boiling point is 83° C. at 0.4 mm Hg. The structural formula of 2-cyclopent-1-enyl-2-(2-methylprop-2-enyl)cyclopentan-1-one is shown in FIG. 2d.

500 Mhz ¹H-NMR (in CDCl₃): δ1.60 (s, 1H), 1.74–1.88 (m, 5H), 2.06–2.14 (m, 1H), 2.17–2.34 (m, 7H), 2.39 (d, 1H), 4.63 (s, 1H), 4.74 (s, 1H), 5.50 (s, 1H).

125 Mhz ¹³C-NMR (in CDCl₃): δ18.90, 23.46, 23.98, 31.82, 32.55, 33.47, 37.26, 42.73, 55.19, 114.10, 127.25, 142.77, 142.83, 218.44.

IR (ν_max(cm⁻¹)): 890(m), 1040(w), 1150(m), 1450(w), 1645(m), 1740(s), 2950(s), 3075(w).

MS(m/z): 204(M⁺), 189, 171, 161, 149, 133, 119, 105, 91, 79, 65, 55, 41.

Embodiment 5

Preparation of 2-cyclopent-1-enyl-2-(2-methylpropyl)-cyclopentan-1-one

This material was prepared as described for Embodiment 1, except that isobutyl bromide was used in place of allyl chloride. From 2-cyclopentylidenecyclopentan-1-one (7.05 g, 0.047 moles) 2-cyclopent-1-enyl-2-(2-methylpropyl)cyclopentan-1-one (4.50 g, 46.4% yield) was obtained.

Figure 2E:
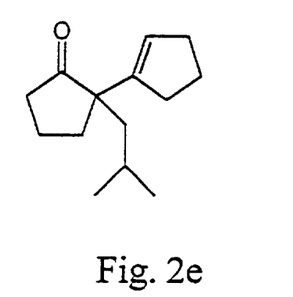
FIG. 2e shows the structural formula of Embodiment 5.

The molecular formula is $C_{14}H_{22}O$, and the molecular weight is 206.33. The boiling point is 90° C. at 0.5 mm Hg. The structural formula of 2-cyclopent-1-enyl-2-(2-methylpropyl)cyclopentan-1-one is shown in FIG. 2e.

500 Mhz ¹H-NMR (in CDCl₃): δ0.82 (d, 3H), 0.87 (d, 3H), 1.18 (dd, 1H), 1.51–1.57 (m, 1H), 1.77–1.90 (m, 6H), 2.07–2.35 (m, 7H), 5.54 (t, 1H).

125 Mhz ¹³C-NMR (in CDCl₃); δ19.17, 23.51, 23.77, 24.49, 25.24, 31.80, 32.57, 34.32, 37.15, 43.59, 55.71, 127.23, 142.56, 219.27.

IR (ν_max(cm⁻¹)): 1040(w), 1150(m), 1470(m), 1630(w), 1740(s), 2960(s), 3060(w).

MS (m/z): 206 (M⁺), 191, 163, 150, 135, 121, 108, 93, 79, 67, 55, 41.

Embodiment 6

Preparation of 2-cyclopentyl-2-(2-methylpropyl)-cyclopentan-1-one

A solution of the compound of Embodiment 4 (2-cyclopent-1-enyl-2-(2-methylprop-2-enyl)cyclopentan-1-one, 5.0 g, 0.02 moles) in ethyl acetate/ethanol (9:1, 100 mL) was added to a Parr reaction bottle. To this vessel was added 5% Pd—C (0.5 g) in one portion. The reaction vessel was placed in a Parr hydrogenation apparatus and H₂ gas (40 psi) was introduced. The apparatus was agitated for 2 hours, and it was determined by TLC and GC that the reaction was complete. The resulting organic slurry was filtered through celite and concentrated. The pale yellow oil was distilled under vacuum to give 2-cyclopentyl-2-(2-methylpropyl)-cyclopentan-1-one (4.24 g, 83.1% yield).

Figure 2F:
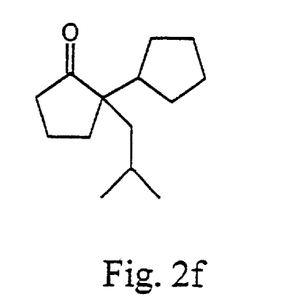
FIG. 2f shows the structural formula of Embodiment 6.

The molecular formula is $C_{14}H_{24}O$, and the molecular weight is 208.35. The boiling point is 88° C. at 0.5 mm Hg. The structural formula of 2-cyclopentyl-2-(2-methylpropyl)-cyclopentan-1-one is shown in FIG. 2f.

500 Mhz ¹H-NMR (in CDCl₃): δ0.78 (d, 3H), 0.85 (d, 3H), 1.05–1.22 (m, 2H), 1.42 (d, 2H), 1.44–1.58 (m, 5H), 1.62–1.72 (m, 2H), 1.81–1.90 (m, 4) 1.99–2.07 (m, 1H), 2.13–2.21 (m, 1H), 2.24–2.32 (m, 1H).

125 Mhz ¹³C-NMR (in CDCl₃); δ18.90, 24.27, 24.61, 25.12, 25.32, 25.32, 27.38, 27.84, 30.96, 39.26, 44.92, 45.59, 53.76, 224.29.

IR (ν_max(cm⁻¹)): 920(w), 1110(m), 1160(m), 1270(w), 1370(w), 1410(w), 1450(m), 1470(m), 1735(s), 2875(s), 2960(s).

MS (m/z): 208 (M⁺), 193, 152, 140, 134, 123, 110, 97, 91, 81, 67, 55, 41.

Embodiment 7

Preparation of 2-cyclopent-1-enyl-2-(3-methylbut-2-enyl)-cyclopentan-1-one

This material was prepared as described for Embodiment 1, except that prenyl bromide was used in place of allyl chloride. From 2-cyclopentylidenecyclopentan-1-one (10.0 g, 0.067 moles) 2-cyclopent-1-enyl-2-(3-methylbut-2-enyl) cyclopentan-1-one (5.64 g, 38.7% yield) was obtained.

Figure 2G:
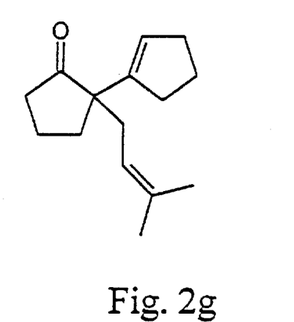
FIG. 2g shows the structural formula of Embodiment 7.

The molecular formula is $C_{15}H_{22}O$, and the molecular weight is 218.34. The boiling point is 90° C. at 0.2 mm Hg. The structural formula of 2-cyclopent-1-enyl-2-(3-methylbut-2-enyl)cyclopentan-1-one is shown in FIG. 2g.

500 Mhz ¹H-NMR (in CDCl₃): δ1.58 (s, 3H), 1.66 (s, 31H), 1.78–1.87 (m, 5H), 2.08–2.19 (m, 3H), 2.24–2.37 (m, 6H), 4.95 (t, 1H), 5.48 (bs, 1H).

125 Mhz $^{13}$C-NMR (in CDCl$_3$): δ18.00, 19.16, 23.45, 25.95, 31.94, 32.51, 33.03, 33.45, 37.98, 55.56, 119.98, 126.78, 133.96, 143.34, 219.70.

IR ($v_{max}$(cm$^{-1}$)) 1040 (w), 1150 (m), 1450 (m), 1630 (w), 1740 (s), 2960 (s), 3050 (w).

MS (m/z): 218 (M$^+$), 203, 150, 119, 105, 91, 84, 79, 69, 41.

Embodiment 8

Preparation of 2-cyclopent-1-enyl-2-(3-methylbutyl)-cyclopentan-1-one

This material was prepared as described for Embodiment 1, except that isoamyl bromide was used in place of allyl chloride. From 2-cyclopentylidenecyclopentan-1-one (15.1 g, 0.10 moles) 2-cyclopent-1-enyl-2-(3-methylbutyl)cyclopentan-1-one (7.84 g, 35.6% yield) was obtained.

Figure 2H:
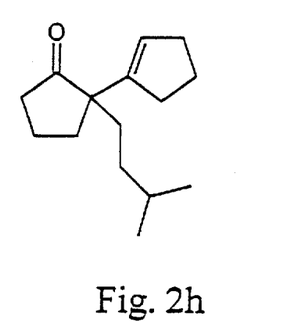
FIG. 2h shows the structural formula of Embodiment 8.

The molecular formula is C$_{15}$H$_{24}$O, and the molecular weight is 220.36. The boiling point is 98° C. at 0.25 mm Hg. The structural formula of 2-cyclopent-1-enyl-2-(3-methylbutyl)cyclopentan-1-one is shown in FIG. 2h.

500 Mhz $^1$H-NMR (in CDCl$_3$): δ0.84 (d, 6H), 0.90 (m, 2H), 1.30 (dt, 1H), 1.39–1.48 (m, 1H), 1.66–1.90 (m, 6H), 2.09–2.35 (m, 7H), 5.50 (t, 1H).

125 Mhz $^{13}$C-NMR (in CDCl$_3$): δ19.15, 22.54, 22.70, 23.47, 28.55, 31.80, 32.50, 32.85, 33.74, 33.88, 37.85, 55.30, 126.90, 142.90, 219.65.

IR ($v_{max}$(cm$^{-1}$)): 820(w), 1045(w), 1150(m), 1375(w), 1470(m), 1640(w), 1740(s), 2875(s), 2960(s), 1060(w).

MS (m/z): 220 (M$^+$), 202, 187, 164, 150, 121, 108, 93, 79, 67, 55, 41.

Embodiment 9

Preparation of 2-cyclopentyl-2-(3-methylbutyl)-cyclopentan-1-one

This material was prepared as described for Embodiment 6, except the cycloalkanone starting material was different. From 2-cyclopent-1-enyl-2-(3-methylbutyl)-cyclopentan-1-one (5.0 g, 0.023 moles) 2-cyclopentyl-2-(3-methylbutyl)-cyclopentan-1-one (4.20 g, 83.2% yield) was obtained.

Figure 2I:
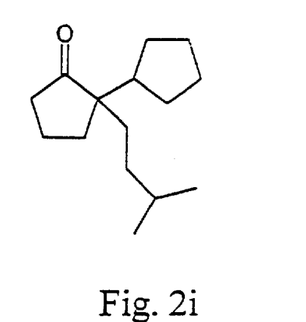
FIG. 2i shows the structural formula of Embodiment 9.

The molecular formula is C$_{15}$H$_{26}$O, and the molecular weight is 222.37. The boiling point is 98° C. at 0.2 mm Hg. The structural formula of 2-cyclopentyl-2-(3-methylbutyl)-cyclopentan-1-one is shown in FIG. 2i.

500 Mhz $^1$H-NMR (in CDCl$_3$): δ0.84 (d, 6H), 0.99–1.24 (m, 4H), 1.36–1.60 (m, 8H), 1.65–1.72 (m, 1H), 1.74–1.92 (m, 4H), 2.02–2.29 (m, 3H).

125 Mhz $^{13}$C-NMR (in CDCl$_3$): δ19.14, 22.65, 25.20, 25.39, 27.51, 27.82, 28.78, 30.94, 33.37, 33.37, 34.56, 39.64, 44.85, 53.69, 224.40.

IR ($v_{max}$(cm$^{-1}$)): 925(w), 1000(w), 1110(w), 1165(m), 1365(w), 1410(w), 1450(m), 1470(m), 1735(s), 2875(s), 2960(s).

MS (m/z): 222 (M$^+$), 207, 179, 154, 152, 134, 123, 110, 97, 84, 79, 67, 55, 41.

Embodiment 10

Preparation of 2-cyclohex-1-enyl-2-prop-2-enylcyclohexan-1-one

This material was prepared as described for Embodiment 1, except that the cycloalkanone starting material was different. From 2-cyclohexylidenecyclohexan-1-one (purchased from Lancaster Synthesis Inc.; 25.0 g, 0.140 moles) 2-cyclohex-1-enyl-2-prop-2-enylcyclohexan-1-one (20.7 g, 67.7% yield) was obtained.

Figure 2J:
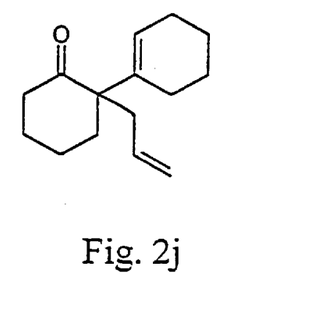
FIG. 2j shows the structural formula of Embodiment 10.

The molecular formula is C$_{15}$H$_{22}$O, and the molecular weight is 218.34. The boiling point is 92° C. at 0.4 mm Hg. The structural formula of 2-cyclohex-1-enyl-2-prop-2-enylcyclohexan-1-one is shown in FIG. 2j.

500 Mhz $^1$H-NMR (in CDCl$_3$): δ1.33 (dt, 1H), 1.46–1.64 (m, 6H), 1.67–1.77 (m, 1H), 1.87–1.98 (m, 2H), 2.01–2.13 (m, 4H), 2.18–2.27 (m, 2H), 2.37 (dd, 1H), 2.47 (dt, 1H), 4.90–4.95 (m, 2H), 5.47 (t, 1H), 5.58–5.67 (m, 1H).

125 Mhz $^{13}$C-NMR (in CDCl$_3$); δ21.70, 22.33, 23.10, 25.21, 25.61, 28.01, 34.64, 40.26, 40.68, 58.03, 116.60, 124.78, 135.27, 135.73, 214.16.

IR ($v_{max}$(cm$^{-1}$)): 905(s), 1000(m), 1120(m), 1320(m), 1450(s), 1640(m), 1705(s), 2860(s), 2950(s), 3080(w).

MS (m/z): 218 (M$^+$), 203, 177, 105, 91, 81, 67, 41.

Embodiment 11

Preparation of 2-cyclohex-1-enyl-2-(2-methylprop-2-enyl)-cyclohexan-1-one

This material was prepared as described for Embodiment 1, except that the cycloalkanone starting material was different, and methallyl chloride was used in place of allyl chloride. From 2-cyclohex-1-enyl-2-(2-methylprop-2-enyl)-cyclohexan-1-one (purchased from Lancaster Synthesis Inc.; 25.0 g, 0.140 moles) 2-cyclohex-1-enyl-2-(2-methylprop-2-enyl)-cyclohexan-1-one (15.4 g, 47.3% yield) was obtained.

Figure 2K:
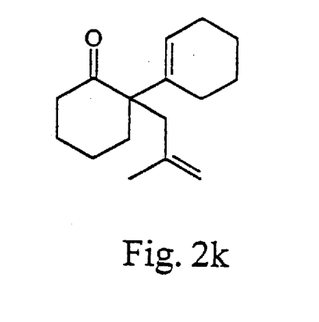
FIG. 2k shows the structural formula of Embodiment 11.
Figure 3A:
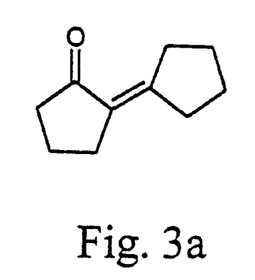
FIG. 3a shows the structural formula of prior art compound pa-1.
Figure 3B:
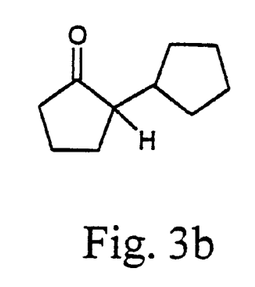
FIG. 3b shows the structural formula of prior art compound pa-2.
Figure 3C:
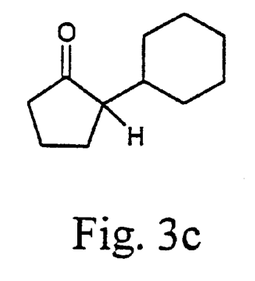
FIG. 3c shows the structural formula of prior art compound pa-3.
Figure 3D:
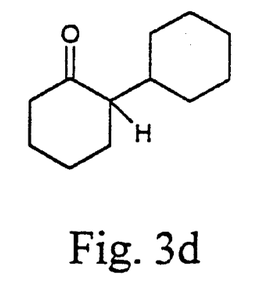
FIG. 3d shows the structural formula of prior art compound pa-4.

The molecular formula is C$_{16}$H$_{24}$O, and the molecular weight is 232.37. The boiling point is 100° C. at 0.4 mm Hg. The structural formula of 2-cyclohex-1-enyl-2-(2-methylprop-2-enyl)-cyclohexan-1-one is shown in FIG. 2k.

500 Mhz $^1$H-NMR (in CDCl$_3$): δ1.33 (dt, 1H), 1.50–1.60 (m, 7H), 1.62 (s, 3H), 1.76 (m, 1H), 1.92–2.23 (m, 6H), 2.35 (dq, 1H), 2.40 (d, 1H), 2.46 (dt, 1H), 4.55 (s, 1H), 4.75 (s, 1H), 4.51 (t, 1H).

125 Mhz $^{13}$C-NMR (in CDCl$_3$): 21.84, 22.21, 23.09, 24.82, 25.38, 25.72, 27.90, 34.59, 40.17, 43.34, 57.91, 114.40, 124.95, 135.54, 142.94, 214.07.

IR ($v_{max}$(cm$^{-1}$)): 580(m), 890(s), 1120(m), 1130(m), 1450 (s), 1645(m), 1710(s), 2850(s), 2950(s), 3080(w).

MS (m/z): 232 (M$^+$), 217, 203, 189, 177, 147, 131, 119, 105, 91, 79, 67, 55, 41.

Measurement of Odor Characteristics

The odor characteristics of Embodiments 1–11 and prior art compounds pa-1, pa-2, pa-3 and pa-4 were assessed by a panel of odor experts. Prior art compounds pa-1, pa-2, pa-3 and pa-4 are monosubstituted cycloalkanones whose structures are shown in FIG. 3. The results of these assessments are shown in Table 1.

TABLE 1

| Embodiment | CAS # | Odor descriptions | Suitable for use in consumer products? |
|---|---|---|---|
| 1 | 7011-72-5 | green, minty, fresh, spicy | Yes |
| 2 | 43011-75-2 | slightly solventy, tea-like | Yes |
| 3 | 100519-76-4 | camphoraceous | Yes |
| 4 | | green, floral, fruity | Yes |
| 5 | | fruity, floral, woody | Yes |
| 6 | | fruity, floral, woody | Yes |
| 7 | | green, floral, fruity | Yes |
| 8 | | woody, fruity | Yes |
| 9 | | fruity, waxy, peach-like | Yes |
| 10 | 4368-58-5 | fruity, floral, woody | Yes |
| 11 | | green, floral, fruity | Yes |
| pa-1 | 825-25-2 | nutty, sweet, woody | No |

TABLE 1-continued

| Embodiment | CAS # | Odor descriptions | Suitable for use in consumer products? |
|---|---|---|---|
| pa-2 | 4884-24-6 | solventy, ketone, acetone-like | No |
| pa-3 | 1502-22-3 | herby, dill, d-carvone-like | No |
| pa-4 | 90-42-6 | herbaceous, minty, sweet | Yes |

Table 1 shows that there are unpredictable differences among the embodiments. For example, both Embodiments 5 and 6 were described as being fruity, floral, and woody. The compounds of Embodiments 5 and 6 differ only in the presence of a double bond in one of the cyclopentane rings. However, Embodiments 8 and 9 differ in the same way, yet Embodiment 8 was described as being woody and fruity, while Embodiment 9 was described as being fruity, waxy, and peach-like. Embodiments 4, 7, and 11 all were described as being green, floral, and fruity, yet no common structural element is present in these compounds. The presence of a double bond on the R group of Embodiment 4 was sufficient to alter its character from fruity, floral, and woody (see Embodiment 5) to green, floral, and fruity, even though the remainder of the compound was identical to the compound of Embodiment 5. Hence, very similar compounds had different odor qualities, and these qualities were not predictable from the structures of the compounds.

Nonetheless, the odor qualities of the embodiments of the present invention, as a whole, were significantly different from those of the prior art compounds. The odor qualities of the various prior art compounds were generally unsuitable for use as fragrance materials. For example, pa-2 has an overpowering solventy, ketone, acetone-like quality that renders it unsuitable for fragrance compositions. A similar fragrance quality is exhibited by pa-3. Pa-1, while not as unpleasant as pa-2, still was judged unsuitable for use in consumer products. Pa-4, while suitable for use in some consumer products, nonetheless exhibited fragrance qualities that were significantly different from those of the present invention.

Preparation of Fragrance Compositions

Two different fragrance compositions were prepared which included compounds of the present invention. The formulae of the fragrance compositions are given below.

TABLE 2

Fragrance Composition GL-GRFL-046

| Ingredient | Formula Parts | % (w/w) |
|---|---|---|
| 2-cyclopent-1-enyl-2-(2-methylprop-2-enyl)cyclopentan-1-one | 150.0 | 18.75 |
| Aldehyde C12 lauric @ 10% DPG | 2.0 | 0.25 |
| Amyl salicylate | 10.0 | 1.25 |
| Benzyl acetate | 30.0 | 3.75 |
| Hedione | 50.0 | 6.25 |
| Heliobouquet | 5.0 | 0.63 |
| Hexyl cinnamic aldehyde | 50.0 | 6.25 |
| Indole crystal @ 10% DPG | 20.0 | 2.50 |
| iso cyclo citral | 5.0 | 0.63 |
| Kovanol (TIC) | 50.0 | 6.25 |
| 1-laurinal | 20.0 | 2.50 |
| Linalool (synthetic) | 50.0 | 6.25 |
| Methyl eugenol | 5.0 | 0.63 |
| Petitgrain oil bigrade | 5.0 | 0.63 |
| Rose accord | 298.0 | 37.25 |
| Suzaral (TIC) | 40.0 | 5.00 |
| Triplal | 10.0 | 1.25 |

TABLE 3

Fragrance Composition GL-HERB-051

| Ingredient | Formula Parts | % (w/w) |
|---|---|---|
| 2-cyclopent-1-enyl-2-prop-2-enylcyclopentan-1-one | 150.0 | 21.43 |
| Armoise oil | 7.5 | 1.07 |
| Benzyl salicylate | 10.0 | 1.43 |
| Cedramber | 5.0 | 0.71 |
| Coumarin | 20.0 | 2.86 |
| Eucalyptus oil | 5.0 | 0.71 |
| Hexenyl salicylate, cis-3 | 20.0 | 2.86 |
| Hexyl salicylate | 100.0 | 14.29 |
| Lavandin grosso | 30.0 | 4.29 |
| Linalool (synthetic) | 42.5 | 6.07 |
| Muguet accord | 160.0 | 22.86 |
| Musk-T | 50.0 | 7.14 |
| Orange oil pera brazil | 40.0 | 5.71 |
| Vertenex | 60.0 | 8.57 |

It is to be understood that the various fragrances described above may be combined with various surfactants and other components of consumer products so that consumer products including the fragrances may be made as desired.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A fragrance composition comprising a disubstituted cycloalkanone of the following general formula (I) or (II):

wherein $R^1$ is a member selected from the group consisting of a straight-chain saturated hydrocarbon group, a branched saturated hydrocarbon group, a straight-chain unsaturated hydrocarbon group, and a branched unsaturated hydrocarbon group, and wherein $R^1$ has from 2 to 6 carbon atoms, and wherein m and n are each either 1 or 2.

2. A fragrance composition comprising a disubstituted cycloalkanone of the following general formula (I) or (II):

-continued (II)

wherein R¹ is a member selected from the group consisting of a straight-chain saturated hydrocarbon group, a branched saturated hydrocarbon group, a straight-chain unsaturated hydrocarbon group, a branched unsaturated hydrocarbon group, wherein R¹ has from 1 to 6 carbon atoms, and wherein m and n each are 1.

3. A fragrance composition according to claim 1, wherein m and n each are 2.

4. A fragrance composition comprising a disubstituted cycloalkanone of the following general formula (I) or (II):

(I)

(II)

wherein R¹ member selected from the group consisting of a straight-chain saturated hydrocarbon group, a branched saturated hydrocarbon group, a straight-chain unsaturated hydrocarbon group, and a branched unsaturated hydrocarbon group, and wherein R¹ has from 1 to 6 carbon atoms; and
wherein m is 1 and n is 2.

5. A fragrance composition comprising a disubstituted cycloalkanone of the following general formula (I) or or (II):

(I)

(II)

wherein R¹ is a member selected from the group consisting of a straight-chain saturated hydrocarbon group a branched saturated hydrocarbon group, a straight-chain unsaturated hydrocarbon group, and a branched unsaturated hydrocarbon group, and wherein R¹ has from 1 to 6 carbon atoms; and
wherein m is 2 and n is 1.

6. A fragrance composition according to claim 1, wherein R¹ is from 3 to 6.

7. A fragrance composition according to claim 1, wherein said disubstituted cycloalkanone is prepared from at least one member selected from the group consisting of 2-cyclopentylidenecyclopentan-1-one, 2-cyclohexylidenecyclohexan-1-one, 2-cyclopentylidenecyclohexan-1-one, and 2-cyclohexylidenecyclopentan-1-one.

8. A fragrance composition according to claim 1, wherein said disubstituted cycloalkanone is a member selected from the group consisting of 2-cyclopent-1-enyl-2-prop-2-enylcyclopentan-1-one, 2-cyclopent-1-enyl-2-ethylcyclopentan-1-one, 2-cyclopent-1-enyl-2-(2-methylprop-2-enyl)cyclopentan-1-one, 2-cyclopent-1-enyl-2-(2-methylpropyl)cyclopentan-1-one, 2-cyclopentyl-2-(2-methylpropyl)-cyclopentan-1-one, 2-cyclopent-1-enyl-2-(3-methylbut-2-enyl)cyclopentan-1-one, 2-cyclopent-1-enyl-2-(3-methylbutyl)cyclopentan-1-one, 2-cyclopentyl-2-(3-methylbutyl)-cyclopentan-1-one, 2-cyclohex-1-enyl-2-prop-2-enylcyclohexan-1-one, and 2-cyclohex-1-enyl-2-(2-methylprop-2-enyl)-cyclohexan-1-one.

9. A fragrance composition comprising at least one disubstituted cycloalkanone of the following general formula (I) or (II):

(I)

(II)

wherein R¹ is a member selected from the group consisting of a straight-chain saturated hydrocarbon group, a branched saturated hydrocarbon group, a straight-chain unsaturated hydrocarbon group, and a branched unsaturated hydrocarbon group, and wherein R¹ has from 1 to 6 carbon atoms, and wherein m and n are each 1 or 2; and a surfactant to form a product, whereby said product is effective to act as at least one of a fragrance, a cleaning agent, a skin cream, a hand and body lotion, a sunscreen agent, a hair conditioner, a water-based adhesive, a water-based paint, a shampoo, a dish washing liquid, a heavy duty cleaner, a general purpose cleaner, a liquid abrasive cleaner, a liquid soap, laundry detergent, deodorant, antiperspirant, bleach, air products, and a fabric softener.

10. A fragrance composition comprising at least one disubstituted cycloalkanone of the following general formula (I) or (II):

(I)

(II)

wherein R¹ is a member selected from the group consisting of a straight-chain saturated hydrocarbon group, a branched saturated hydrocarbon group, a straight-chain unsaturated hydrocarbon group, and a branched unsaturated hydrocarbon group, and wherein R¹ has from 1 to 6 carbon atoms and wherein m and n are each either 1 or 2;

wherein said disubstituted cycloalkanone is prepared from at least one member selected from the group consisting of 2-cyclopentylidenecyclopentan-1-one, 2-cyclohexylidenecyclohexan-1-one, 2-cyclopentylidenecyclohexan-1-one, and 2-cyclohexylidenecyclopentan-1-one, and a surfactant to form a product, whereby said product is effective to act as at least one of a fragrance, a cleaning agent, a skin cream, a hand and body lotion, a sunscreen agent, a hair conditioner, a water-based adhesive, a water-based paint, a shampoo, a dish washing liquid, a heavy duty cleaner, a general purpose cleaner, a liquid abrasive cleaner, a liquid soap, laundry detergent, deodorant, antiperspirant, bleach, air care products, and a fabric softener.

11. A fragrance composition comprising at least one disubstituted cycloalkanone selected from the group consisting of 2-cyclopent-1-enyl-2-prop-2-enylcyclopehtan-1-one, 2-cyclopent-1-enyl-2-methylcyclopentan-1-one, 2-cyclopent-1-enyl-2-ethylcyclopentan-1-one, 2-cyclopent-1-enyl-2-(2-methylprop-2-enyl)cyclopentan-1-one, 2-cyclopent-1-enyl-2-(2-methylpropyl)cyclopentan-1-one, 2-cyclopentyl-2-(2-methylpropyl)-cyclopentan-1-one, 2-cyclopent-1-enyl-2-(3-methylbut-2-enyl)cyclopentan-1-one, 2-cyclopent-1-enyl-2-(3-methylbutyl)cyclopentan-1-one, 2-cyclopentyl-2-(3-methylbutyl)-cyclopentan-1-one, 2-cyclohex-1-enyl-2-prop-2-enylcyclohexan-1-one, and 2-cyclohex-1-enyl-2-(2-methylprop-2-enyl)-cyclohexan-1-one; and a surfactant to form a product, whereby said product is effective to act as at least one of a fragrance, a cleaning agent, a skin cream, a hand and body lotion, a sunscreen agent, a hair conditioner, a water-based adhesive, a water-based paint, a shampoo, a dish washing liquid, a heavy duty cleaner, a general purpose cleaner, a liquid abrasive cleaner, a liquid soap, laundry, detergent, deodorant, antiperspirant, bleach, air care products, and a fabric softener.

* * * * *

UNITED STATES PATENT AND TRADEMARK OFFICE
CERTIFICATE OF CORRECTION

PATENT NO.    : 6,548,474 B1
DATED         : April 15, 2003
INVENTOR(S)   : Carter B. Green et al.

It is certified that error appears in the above-identified patent and that said Letters Patent is hereby corrected as shown below:

<u>Title page,</u>
Item [73], Assignee, delete "Takasago Institute for Interdisiplinary Science Inc." and substitute with -- Takasago Institute for Interterdisciplinary Science Inc. --.

Signed and Sealed this

Second Day of September, 2003

JAMES E. ROGAN
*Director of the United States Patent and Trademark Office*